United States Patent
Tharpe, Jr. et al.

(10) Patent No.: US 6,334,900 B2
(45) Date of Patent: *Jan. 1, 2002

(54) APPARATUS FOR APPLYING A GEL PREPARATION TO DISPOSABLE PRODUCTS

(76) Inventors: John M. Tharpe, Jr., 1610 Louise Ave., Panama City, FL (US) 32401; William L. Meadow, 1805 Gail Ave., Albany, GA (US) 31707

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/164,612

(22) Filed: Oct. 1, 1998

(51) Int. Cl.⁷ .................................................. B05C 5/02
(52) U.S. Cl. ....................... 118/674; 118/679; 118/683; 118/411; 118/412
(58) Field of Search ................................ 118/100, 400, 118/123, 124, 672, 674, 663, 101, 666, 667, 679, 683, 411, 412, 313, 315, 324; 427/355, 369, 370, 792.2, 286, 288; 239/597, 135, 566

(56) References Cited

U.S. PATENT DOCUMENTS

| | | | |
|---|---|---|---|
| 2,033,379 A | * 3/1936 | Jenkins | 118/101 X |
| 2,054,448 A | * 9/1936 | Russell | 118/413 |
| 2,408,504 A | * 10/1946 | Bergsteinn | 118/413 |
| 3,418,970 A | * 12/1968 | Phelps et al. | 118/413 |
| 3,897,578 A | * 7/1975 | Kanda et al. | 118/123 |
| 4,475,478 A | * 10/1984 | Bendinner | 118/413 |
| 5,133,996 A | * 7/1992 | Busker | 118/413 |
| 5,540,774 A | * 7/1996 | Smitherman | 118/315 |

* cited by examiner

Primary Examiner—Laura Edwards
(74) Attorney, Agent, or Firm—Allen, Dyer, Doppelt, Milbrath & Gilchrist, P.A

(57) ABSTRACT

An apparatus for applying a gel onto a sheet of material for production of disposable undergarments, the sheet moving in a predetermined direction of manufacture at a predetermined rate of travel, the apparatus comprising: a container positioned to contain a supply of the gel; a shoe comprising a body having a lower surface, a proximal end positioned to receive the sheet of material as the sheet travels in the predetermined direction of manufacture, and a distal end, an inlet conduit positioned within the body to receive the gel therein, a chamber connected to the inlet conduit and positioned within the body, a groove extending along the lower surface of the body and a plurality of spaced-apart outlet conduits each extending from the chamber to the groove so that the gel is delivered onto the sheet of material in a pattern of substantially parallel lines; and a gel delivery controller positioned in fluid communication with the container and with the shoe, for providing a variably controlled flow of the gel from the container to the inlet conduit of the shoe, therethrough to the chamber and to the plurality of outlet conduits, and therefrom for delivery onto the sheet of material at a rate responsive to the predetermined rate of travel of the sheet of material.

51 Claims, 5 Drawing Sheets

APPARATUS FOR APPLYING A GEL PREPARATION TO DISPOSABLE PRODUCTS

FIELD OF THE INVENTION

The present invention relates to the disposable products industry, particularly to the field of manufacturing disposable undergarments.

BACKGROUND OF THE INVENTION

Consumer demand for disposable undergarments such as diapers or panties has continued to grow since these items were introduced in the market. These products are used on children who are not yet toilet trained, as well as on adults who are fully or partially incontinent due to illness or other medical conditions. Disposable undergarments, diapers and panties in particular, are usually fabricated of at least three layers of material: a barrier bottom layer impervious to liquid; a top porous layer which touches the skin of the wearer and freely allows liquids to pass through; and an inner layer of an absorbent material, positioned between the top and bottom layers for holding fluids discharged by the wearer.

There has been interest in applying emollient preparations and various other products such as creams and petroleum jelly to the layer of the disposable undergarment which goes against the wearer's skin. These products may include creams to fight diaper rash, emollients to aid in keeping the wearer's skin soft, lubricants to help prevent stools from adhering to the skin, antibiotic preparations to control and suppress infections, and others. The application of such products, which are usually soft, cream-like, or jellied preparations, however, poses a technical challenge in the manufacturing process. Generally, these products are semi-solid gels or creams which may be difficult to convey and to apply onto materials moving on a production line. This is particularly true since these soft preparations must be applied to the top layer of the undergarment, so that they will contact the skin of the wearer. For the undergarment to maintain its effectiveness, however, the top layer of the undergarment, which is next to the skin of the wearer, must remain permeable to liquids and cannot be blocked by the application of the gel preparation. Techniques which are well known in the art for applying a gel during the manufacturing process include spraying and deposition through an applicator shoe.

In one known application technique the gel preparation is sprayed onto the material moving on the production line. In order to spray a gel, however, the gel must be heated to the point that it turns liquid. This heating tends to cause some evaporation of the gel and to affect the consistency of the gel upon cooling; the gel becomes harder as more liquid evaporates during this process. In addition, controlled deposition of gel onto the material moving on the production line is difficult when using a spraying process. Spray, particularly a hot spray, tends to spread during application and to run uncontrollably over the material once deposited; this tends to cover the entire surface of the material with liquefied gel. Because the spray covers most of the surface of the material, as the spray cools and the gel forms once again, most of the pores on the material will be clogged with gel and the undergarment's absorbency will be greatly reduced. The undergarment will be less comfortable to the wearer because of its reduced absorbency.

In another known technique the gel may be applied onto the material moving on the production line by deposition through an applicator shoe. This method is well known in the art of manufacturing disposable undergarments. Present applicator shoe designs, however, also tend to spread the gel over most of the surface of the undergarment material. The gel is deposited across most of the width of the material and then is spread over the surface. This method suffers the disadvantages of lack of control over the spread of the gel and of uneven distribution of the gel. This technique also tends to cover most of the pores of the top layer of the undergarment, the top layer being that layer which is next to the wearer's skin. This method of application, therefore, also tends to interfere with the absorbency of the undergarment, resulting in a less effective and less comfortable product.

SUMMARY OF THE INVENTION

In view of the foregoing background, the present invention provides an apparatus and associated methods for applying a gel in a uniformly controlled pattern onto a material moving on a production line. The gel is applied in a pattern that allows the deposition of a sufficient quantity of gel to produce the desired effect when the undergarment is worn but that does not reduce the absorbency of the undergarment. The present invention thereby advantageously provides for manufacturing a disposable undergarment which is more comfortable for the skin of the wearer through the application of a gel, while maintaining the high absorbency of the undergarment.

More particularly, the present invention provides an apparatus for applying a gel onto a material moving on a production line for the production of disposable undergarments. The apparatus preferably has a supply of gel, gel delivering means for delivering the gel in a predetermined and uniformly distributed pattern to the sheet of material, and gel delivering control means positioned in fluid communication with the supply of gel and the gel delivering means for providing a variably controlled flow of the gel through the apparatus and onto the material at a rate responsive to the rate of travel of the material on the production line.

Figure 1:
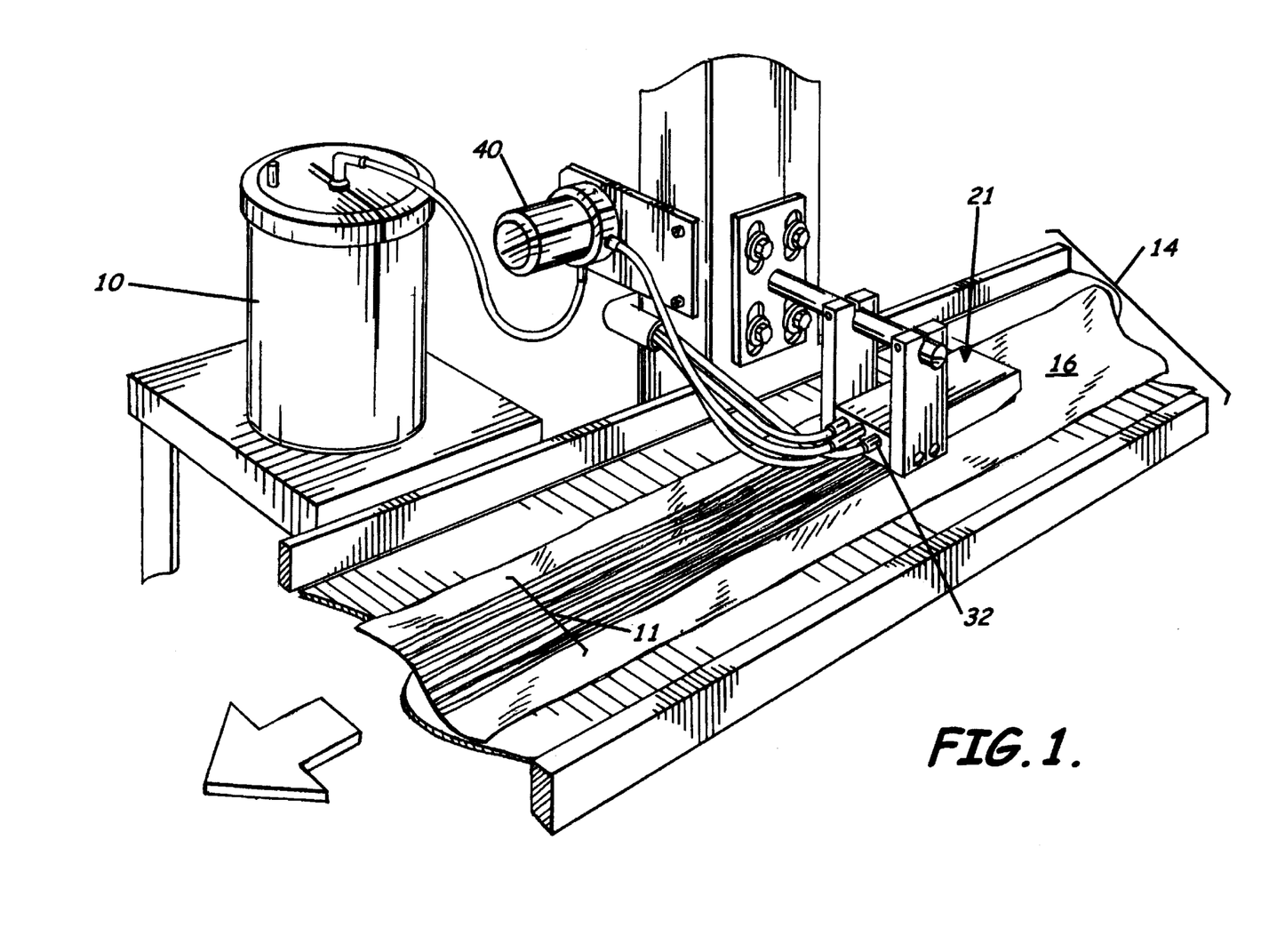
FIG. 1 is a perspective view of the apparatus of the present invention as used on a production line, with the shoe applying a gel to material moving thereon.

The supply of gel is preferably held in a cylindrical container positioned in fluid communication with the gel delivering means and the gel delivering control means. Because the present invention provides the advantage of heating the gel only at delivery through the gel delivery means, the container is not heated but is held at room temperature to avoid undue evaporation of the gel. The relationship of the gel supply container to the other components of the apparatus of the present invention is best shown in FIG. 1.

The gel delivering means preferably includes an applicator shoe, simply known in the art as a "shoe", having a body generally rectangular in shape and which includes an inlet conduit for receiving the gel therein, a chamber connected to the inlet conduit for distributing said gel, a plurality of spaced-apart outlet conduits each extending from the chamber so that the gel is delivered therefrom onto the sheet of material in a pattern of substantially parallel lines. The body of the shoe has a lower surface and a groove extending along a slanted portion of that lower surface at the proximal end of the body of the shoe, the plurality of spaced-apart outlet conduits extending from the chamber to the groove for delivering the gel therefrom. The groove provides the present invention with a further advantage by acting as a pooling area for the gel as it is squeezed out from the plurality of spaced-apart outlet conduits, allowing the gel to flow smoothly and without the formation of globs that would fall onto the material, interfering with the proper deposition of the gel pattern on the material. The shoe has a heater to warm the body of the shoe and thereby promote fluidity of the gel at delivery onto the material. The lower surface of the body of the shoe also includes a horizontal portion which abuttingly overlies the material on the production line as it moves thereon and serves to prolong the warming of the gel after delivery and to allow better absorption of the gel by the material.

The gel delivering control means preferably includes a variable speed pump for conveying the gel through the apparatus and a pump controller connected to the pump for providing regulation of the pump. A further advantage provided by the present invention is gel delivering control in a manner responsive to the rate of movement of the material on the production line. The variable speed pump may be any one of various devices known and used in the art for delivering a measured volume at a given rate, including a gear pump or a peristaltic pump.

The present invention also advantageously provides methods of applying a gel onto a material moving on a production line. A method preferably includes supplying the gel, delivering the gel onto the material in a uniformly distributed pattern, and variably controlling delivery of the gel at a rate related to the predetermined rate of travel of the material. The method also includes delivering the gel onto the material at a rate responsive to the predetermined rate of travel of the material on the production line. The method additionally includes the step of heating the gel during delivery, thereby to reduce the viscosity of the gel and promote controlled delivery.

Another method of applying a gel onto a material moving on a production line according to the present invention includes supplying the gel to a shoe, heating the shoe and delivering the gel from the shoe onto the material moving on the production line. The method further includes the steps of delivering the gel in a uniformly controlled pattern, wherein the rate of delivery is variably controlled responsively to the predetermined rate of travel of the material on the production line.

Yet another method of applying a gel onto a material moving on a production line according to the present invention includes the steps of providing a shoe having an inlet conduit for receiving the gel therein, a chamber connected to the inlet conduit for distributing the gel, a plurality of spaced-apart outlet conduits each extending from the chamber so that the gel is delivered therefrom onto the material in a uniformly distributed pattern and providing a delivery controller positioned in fluid communication with the shoe, for variably controlling flow of the gel to the inlet conduit of the shoe and therefrom onto the material at a rate responsive to the predetermined rate of travel of the material.

Having thus summarized the present invention, a more detailed description will now be provided so that those skilled in the art may more fully appreciate its advantages.

BRIEF DESCRIPTION OF THE DRAWINGS

Some of the features, advantages and benefits of the present invention having been stated, others will become apparent as the description proceeds when taken in conjunction with the accompanying drawings, in which.

DETAILED DESCRIPTION OF A PREFERRED EMBODIMENT

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and double prime notation, if used, indicate similar elements in alternative embodiments.

FIG. 1 illustrates a production line 14 for manufacturing disposable undergarments, particularly showing the apparatus of the present invention for applying a gel 11 onto a sheet of material 16 moving at a predetermined rate on the production line 14. The term "gel" when used herein is intended to include any preparation which is jelly-like, soft or semisolid paste or cream, including a colloid as in the true sense of the word "gel", for example, petroleum jelly and a colloid of *Aloe vera* in petroleum jelly. The apparatus, as shown in FIG. 1, includes a container 10 to hold a supply of gel 11, an applicator shoe 20, and a gel delivery controller 40 mechanism for conveying the gel 11.

The shoe 20 is positioned to abuttingly overlie the sheet of material 16 as the sheet travels in the predetermined direction of manufacture. The shoe 20 has a proximal end 24 to receive the material 16 as it travels on the production line 14 and a distal end 36 from where the material 16 emerges from under the shoe 20. The lower surface of the shoe 20 at the proximal end 24 has a upwardly slanted portion 28 so as to form an entrance area wherein the material is received without snagging under the shoe 20 as the material moves in the direction of manufacture. The various features included in the body 21 of the shoe 20 are best shown in FIGS. 4 through 8. There is an inlet conduit 23, best illustrated in FIG. 5, positioned within the body 21 of the shoe 20 to receive the gel 11 therein. The body 21 of the shoe 20 also has a chamber 38 connected to the inlet conduit 23, a groove 22 extending along the lower surface of the proximal end 24 of the shoe's body 21 and a plurality of spaced-apart outlet conduits 26 each extending from the chamber 38 to the groove 22 for delivering the gel 11 onto the sheet of material 16 in a pattern of parallel lines. The slanted portion 28 of the shoe's lower surface may be constructed having a predetermined inclination relative to the fluidity of the gel 11 being applied, thereby promoting a smooth flow of the gel 11 for delivery onto the material 16. The body 21 of the shoe 20 is heated, so as to promote fluidity in the gel 11 while heating it for a minimal amount of time. The shoe body 21 has receptacles 30 wherein a heater 32 and a temperature sensor are placed, thereby the heating of the shoe 20 is carefully controlled to prevent undue evaporation, separation or other undesirable effects on the gel 11. In the preferred embodiment, the heater 32 is an electric heater 32. The bottom surface of the shoe 20 has a substantially horizontal portion 34 extending from the slanted portion 28 to the distal, or rear, end of the shoe 20. This horizontal portion 34 is heated and abuttingly overlies the material 16 moving on the production line 14. This heated surface helps prolong the more fluid state of the gel 11 after it is delivered onto the material 16, thereby promoting its enhanced absorption by the material 16.

The apparatus also includes a gel delivery controller 40 positioned in fluid communication with the container 10 and the shoe 20, for providing a variably controlled flow of the gel 11 from the container 10 to the inlet conduit 23 of the shoe 20 and therethrough to the chamber 38 and to the plurality of outlet conduits 26, from where it is delivered onto the sheet of material 16 at a rate responsive to the predetermined rate of travel of the sheet of material 16. The gel delivery controller 40 preferably includes a variable speed pump regulated by a speed control mechanism, to deliver the gel 11 through the apparatus and onto the material 16 moving on the production line 14 in a metered amount responsive to the rate of production.

Figures 2, 3:
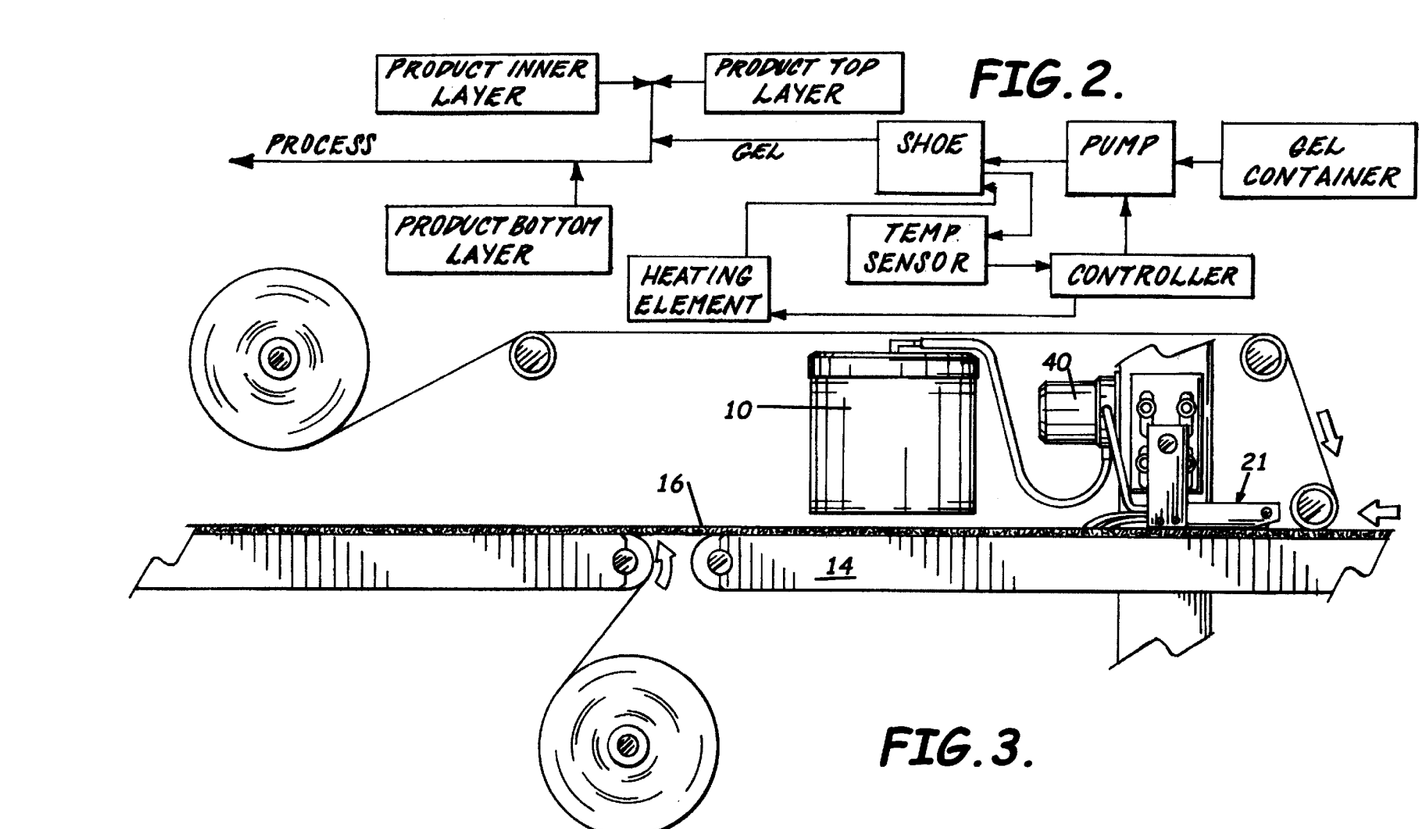
FIG. 2 is a schematic flow diagram of a manufacturing process incorporating the application of the gel through the present invention.
FIG. 3 is a side elevation view of a production line for disposable undergarments showing the components of the present invention in relation to the manufacturing process.

A flow diagram representative of the production process is shown in FIG. 2. The corresponding structural elements of the production process are shown in FIG. 3. The production line 14 is shown in FIG. 3 moving from right to left. The material 16 moves on the production line 14 and passes under the shoe 20, entering under the shoe at the slanted lower surface located at the proximal end 24 of the shoe. The slanted portion 28 of the shoe's undersurface has a groove 22 wherein are located the outlet conduits 26 from which the gel 11 is extruded onto the moving material 16 below in a predetermined pattern which in the preferred embodiment is substantially parallel lines.

Figure 4:
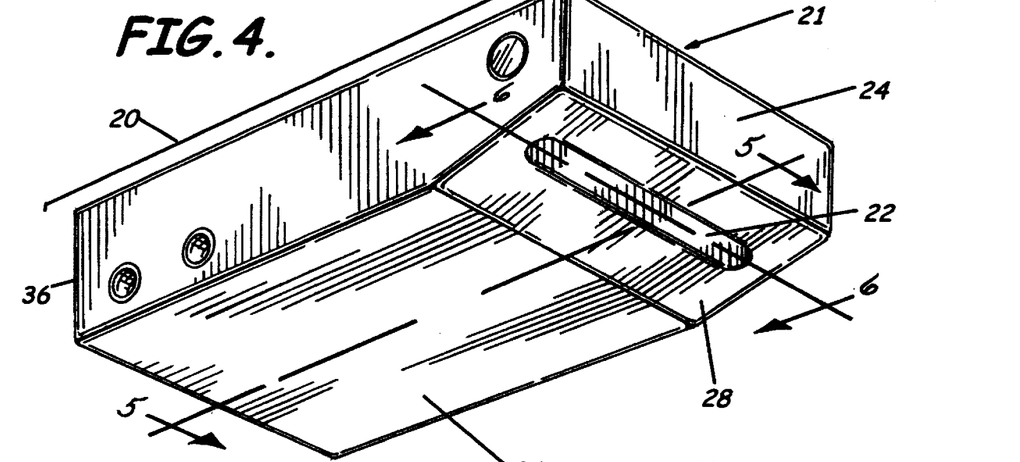
FIG. 4 is a bottom perspective view of the shoe device, providing a detail view of the lower surface of the shoe, including the groove, and the slanted and horizontal portions of the undersurface.
Figure 8:
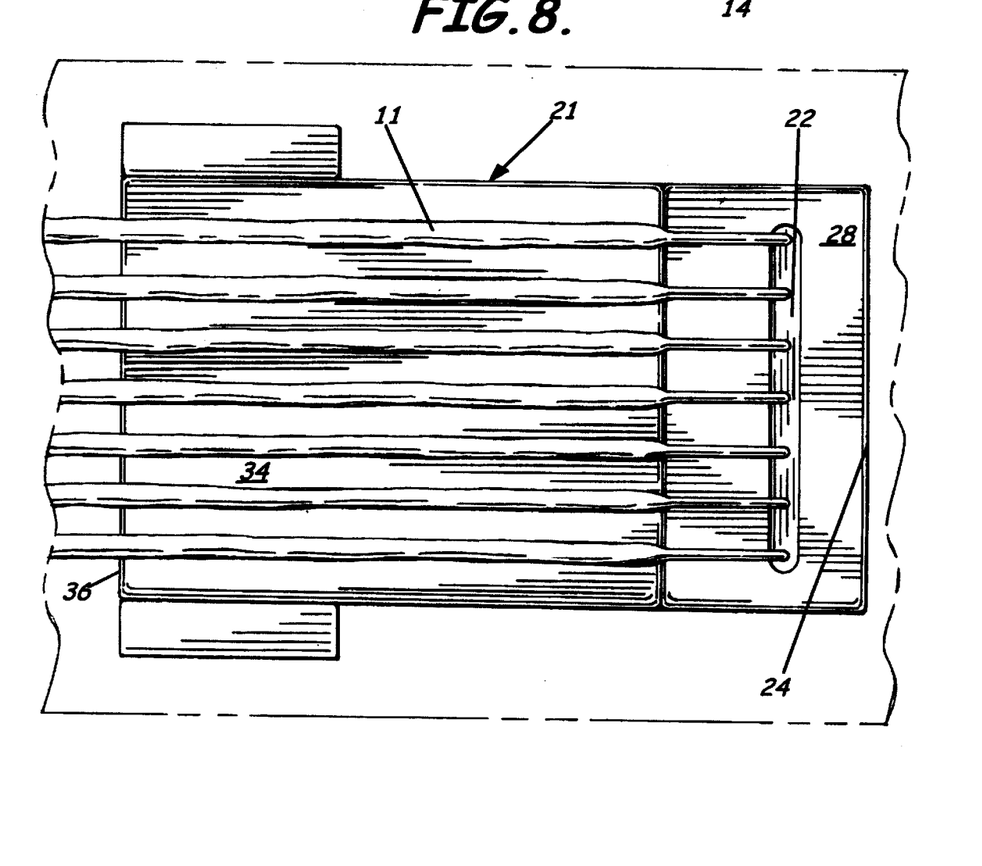
FIG. 8 is a bottom plan view of the shoe as it applies a gel to the material moving on the production line, illustrating how the horizontal portion of the shoe's lower surface by warming the applied gel allows the gel to spread slightly, thereby promoting absorption of the gel by the material.
Figure 9:
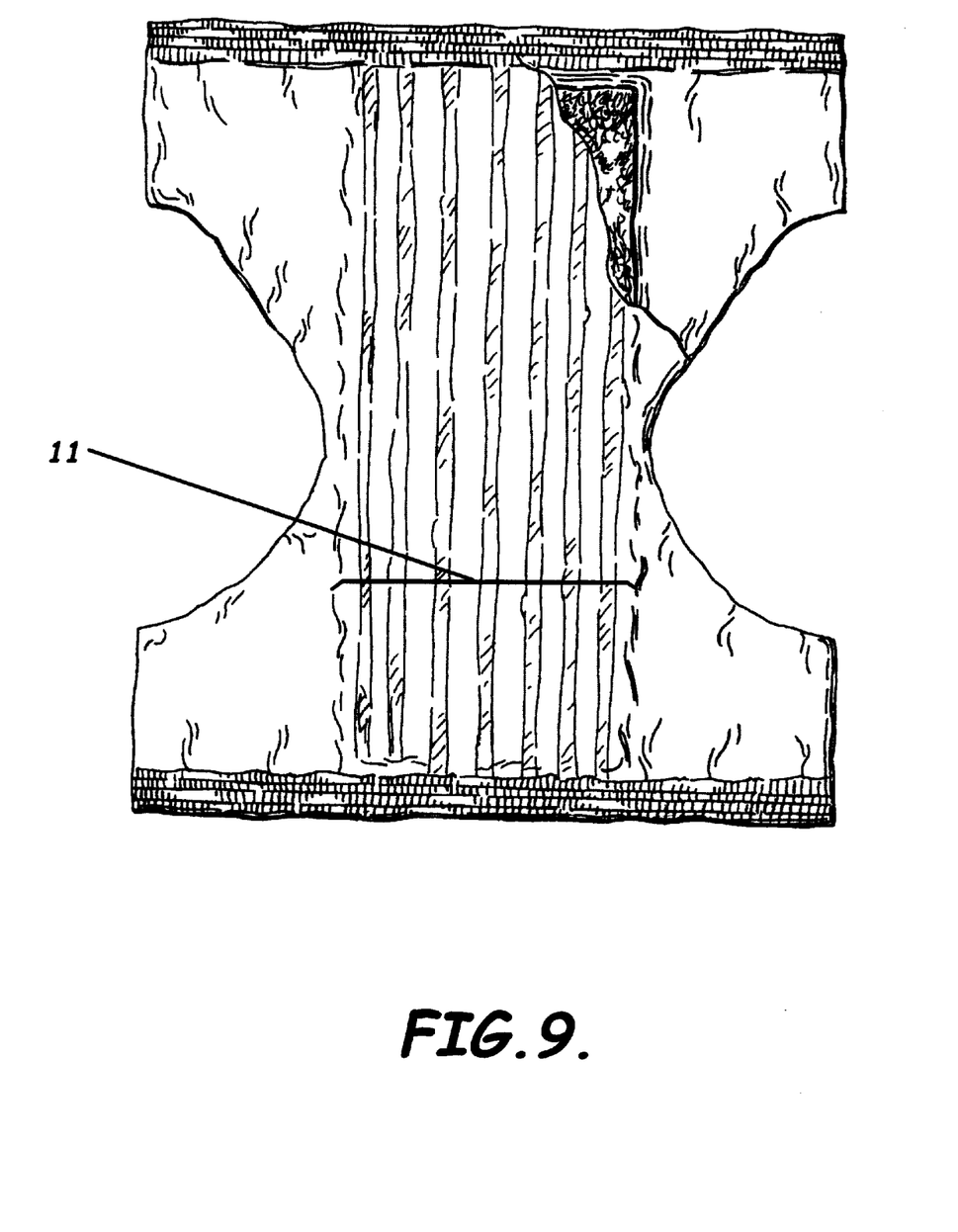
FIG. 9 is a view of a disposable undergarment manufactured through the present invention, showing the applied gel on the finished product.

A perspective bottom view of the shoe 20 is illustrated in FIG. 4, particularly showing the slanted portion 28 of the bottom surface at the proximal end 24 of the shoe 20 and the groove 22 therein. Also shown in FIG. 4 is the substantially horizontal portion 34 of the shoe's lower surface, under which the material 16 slides as it moves on the production line 14. This horizontal portion 34 of the undersurface of the shoe abuttingly overlies the material 16 moving on the production line 14. Because the body 21 of the shoe 20 is heated, this horizontal lower surface of the shoe continues to warm the gel 11 deposited on the material 16 as the production line 14 moves the material 16 under and past the shoe 20. As the shoe 20 continues to keep the deposited gel 11 warm, the gel spreads somewhat but still retains the pattern of substantially parallel lines on the moving material 16, as best shown in FIG. 8. This provides optimal coverage of the material 16 by the gel 11, while maintaining the absorbency of the undergarment.

Figure 5:
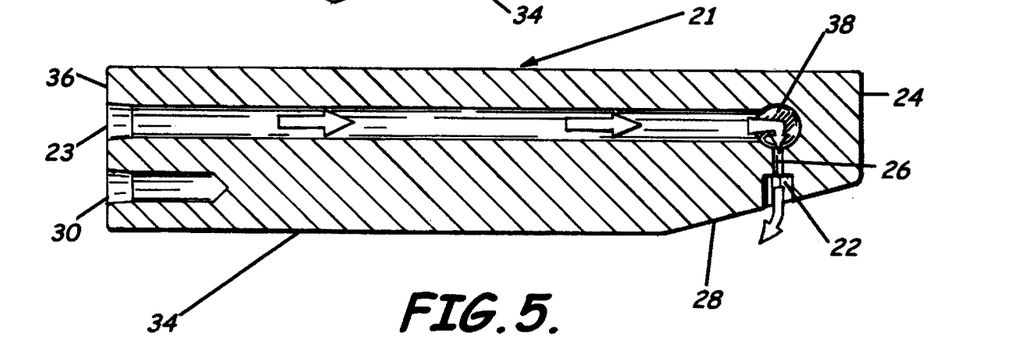
FIG. 5 is a cross sectional view of the shoe device taken along line 5—5 of FIG. 4, showing the inlet conduit, the chamber, an outlet conduit and a receptacle for the temperature sensor.

A cross sectional view of the body 21 of the shoe 20 showing the detail of the inlet conduit 23 is shown in FIG. 5, which is a view taken along the line 5—5 of FIG. 4. The cross section shows the inlet conduit 23 positioned within the body 21 of the shoe 20. The gel 11 is pumped through the inlet conduit 23 to the chamber 38 located above the slanted undersurface at the proximal end 24 of the shoe. From the chamber 38 extend a plurality of spaced-apart outlet conduits 26 each leading downward from the chamber 38 to open within the groove 22 located on the slanted undersurface of the shoe. The gel 11 is delivered from the chamber 38 through the spaced-apart outlet conduits 26 and the groove 22 onto the material 16 moving on the production line 14 below in a pattern of substantially parallel lines.

Figure 6:
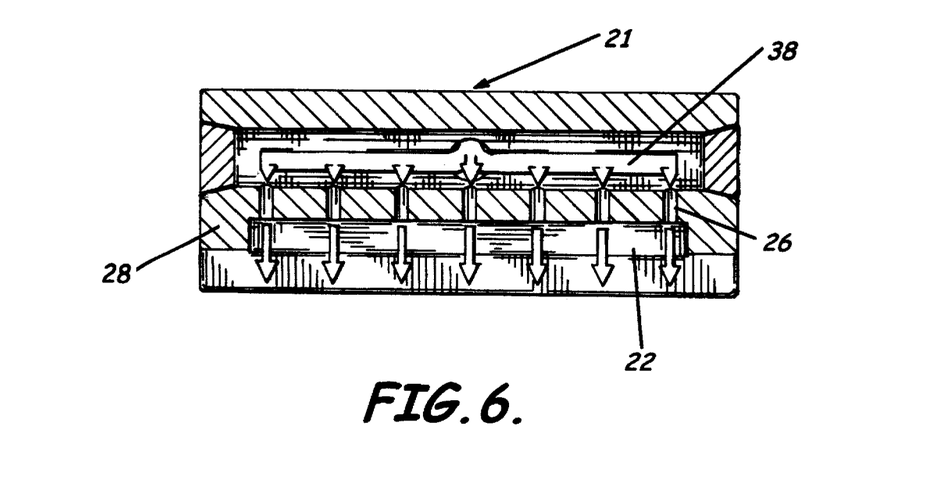
FIG. 6 is a cross sectional view of the shoe device taken at the proximal end along line 6—6 of FIG. 4, illustrating the chamber, the plurality of spaced-apart outlet conduits and the groove on the slanted portion of the shoe's lower surface.

A more detailed view of the relationship of the chamber 38, the spaced-apart outlet conduits 26 and the groove 22 on the slanted portion 28 of the proximal undersurface of the shoe is shown in FIG. 6, which is a cross sectional view taken along the line 6—6 of FIG. 4. The chamber 38 is located within the body 21 of the shoe 20 at the proximal end 24 of the body 21 and communicates with the inlet conduit 23. The chamber 38 provides a space through which the gel 11 entering from the inlet conduit 23 can spread to the plurality of spaced-apart outlet conduits 26, and in that sense the chamber 38 acts as a manifold with one inlet and several outlets. The plurality of spaced-apart outlet conduits 26 lead from the chamber 38 to the groove 22 on the slanted portion 28 of the bottom surface of the shoe 20. This groove 22 on the slanted underportion of the shoe is an important feature in that it provides a pooling area for the gel 11 as it is squeezed out from the plurality of spaced-apart outlet conduits 26. This pooling action allows the gel 11 to continue to flow smoothly and at a controlled rate from the spaced-apart outlet conduits 26 during the operation, without the accumulation of globs of gel 11 that would drop off, interfering with the proper deposition of the gel 11 pattern on the material 16.

Figure 7:
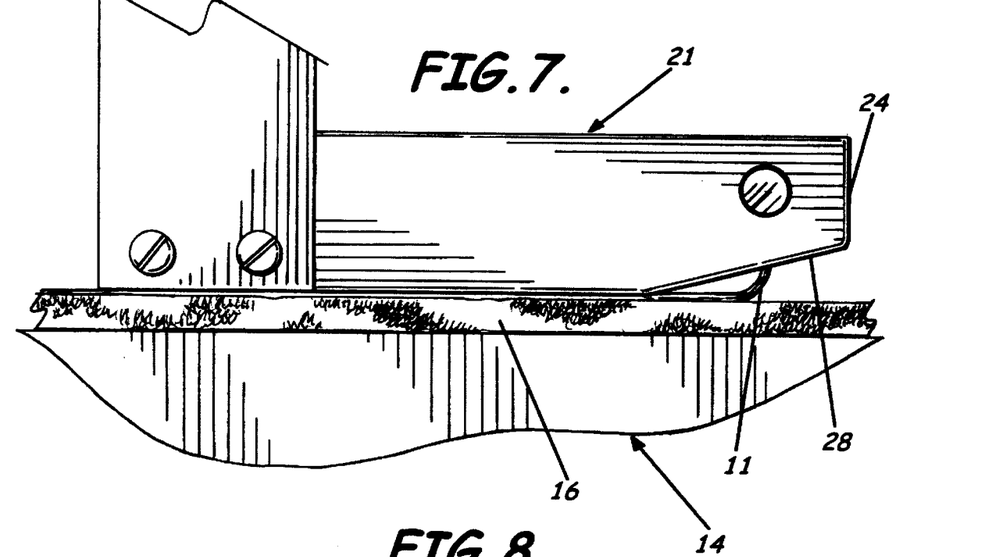
FIG. 7 is an enlarged side elevation view of the shoe in relation to the material moving on the production line, showing the gel being applied onto the material from the slanted portion of the lower surface of the shoe and the horizontal portion of the shoe's lower surface abuttingly overlying the material on the production line.

An enlarged side elevation view of the shoe 20 in relation to the material 16 moving on the production line 14 is shown in FIG. 7. As the production line 14 conveyor moves, the material 16 flows under the shoe 20 by entering below the slanted portion 28 of the shoe's undersurface. While below the shoe's slanted undersurface, the material 16 receives a deposit of the gel 11 as the gel is extruded through the spaced-apart outlet conduits 26 terminating at the groove 22. The material 16 then continues traveling below the shoe 20 and the gel 11 which was deposited as substantially parallel lines is further warmed by the shoe's flat undersurface portion, acting much as a conventional clothes iron but without the shoe 20 exerting a significant compression force against the material 16.

A more detailed view of the shoe 20 as it applies a gel 11 to the material 16 moving on the production line 14 is shown in FIG. 8, which is a bottom plan view of the shoe. This view, as if through a transparent material moving on the production line 14, illustrates how the further warming of the gel 11 by the horizontal portion 34 of the shoe's undersurface promotes a slight spread and absorption of the gel 11 onto the material 16. The warm liquefied gel 11 is absorbed by the material 16 and, as it cools, it once again forms into a gel 11 within the material. This process helps to keep the gel 11 in place on and within the material 16, while also maintaining the parallel line pattern so as not to adversely affect the undergarment's absorbency.

As illustrated in FIGS. 1 through 9, the present invention also includes a method for supplying the gel 11, heating the gel at the point of delivery, and variably controlling delivery of the gel 11 in a uniformly controlled pattern onto a material 16 moving in a predetermined direction of manufacture at a predetermined rate of travel. The method teaches providing a shoe 20 having a body 21 with an inlet conduit 23 for receiving the gel 11 therein, a chamber 38 connected to the inlet conduit 23 for distributing the gel 11 to a plurality of spaced-apart outlet conduits 26 each extending from the chamber 38, so that the gel 11 is delivered from the spaced-apart outlet conduits 26 onto the material 16 in a uniformly distributed pattern. The preferred method teaches heating the gel 11 at the point of delivery onto the material 16 by providing a heater 32 in the body 21 of the shoe 20. The method further calls for providing a gel delivery controller 40 positioned in fluid communication with the shoe 20, for regulating the flow of gel 11 to the inlet conduit 23 of the shoe, therethrough to the chamber 38 and to the spaced-apart outlet conduits 26 from which the gel 11 is delivered through the groove 22 onto the material 16 at a rate responsive to the predetermined rate of travel of the material 16.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. An apparatus for applying a gel onto a sheet of material for production of disposable undergarments, the sheet moving in a predetermined direction of manufacture at a predetermined rate of travel, the apparatus comprising:

a) a container for containing a supply of the gel;
    b) a shoe comprising a body having a lower surface, a proximal end positioned to receive the sheet of material as the sheet travels in the predetermined direction of manufacture, and a distal end, an inlet conduit positioned within the body to receive the gel therein, a chamber connected to the inlet conduit and positioned within the body, a groove extending along the lower surface of the proximal end of the body and a plurality of spaced-apart outlet conduits each extending from said chamber to said groove so that the gel is delivered onto the sheet of material in a pattern of substantially parallel lines; and
    c) a gel delivery controller positioned in fluid communication with said container and with said shoe, for providing a variably controlled flow of the gel from said container to said inlet conduit of said shoe, therethrough to said chamber, said plurality of outlet conduits, and therefrom for delivery onto the sheet of material at a rate responsive to the predetermined rate of travel of the sheet of material.

2. The apparatus of claim 1 wherein the lower surface includes a slanted portion positioned along the proximal end of the body so as to form an entrance area wherein the sheet of material is received to travel without snagging under said shoe as the sheet of material moves in the predetermined direction of manufacture.

3. The apparatus of claim 2 wherein said slanted portion of the lower surface defines a first side of a predetermined angle, and wherein said sheet of material defines a second side of the angle, the angle having an open end at the proximal end of the body of said shoe.

4. The apparatus of claim 3 wherein said predetermined angle is sufficiently wide to allow said sheet of material to be received under said shoe without snagging as the sheet of material travels in the predetermined direction of manufacture.

5. The apparatus of claim 4 wherein the predetermined angle has a range of between 5 degrees to 45 degrees.

6. The apparatus of claim 5 wherein the predetermined angle further comprises the slanted portion of said lower surface having a predetermined inclination relative to the fluidity of the gel, thereby promoting a smooth flow of the gel for delivering onto said sheet of material.

7. The apparatus of claim 4 further comprising heating means for variably and controllably heating of said shoe, to thereby convert the gel to a more fluid state for delivery onto the sheet of material.

8. The apparatus of claim 7 wherein said heating means comprises a heater for heating the body of said shoe, a temperature sensor for sensing the temperature of the body of said shoe, and a temperature controller connected to the heater and to the temperature sensor for controlling the temperature of the body of said shoe.

9. The apparatus of claim 8 wherein said heater is positioned within the body of said shoe, said heater being an electric heater and being electrically connected to said temperature controller.

10. The apparatus of claim 7 wherein said shoe further comprises a substantially horizontal portion of said lower surface, said horizontal portion extending from said slanted portion to said distal end, said horizontal portion being heated and abuttingly overlying the sheet of material traveling in the predetermined direction of production so that the more fluid state of the gel is prolonged after the gel is delivered onto the sheet, to thereby promote enhanced absorption of the gel by the material.

11. The apparatus of claim 10 wherein said gel delivery controller comprises a variable speed pump, to thereby allow for delivery of the gel onto the sheet of material at a volume responsive to the predetermined rate of travel of the sheet of material.

12. The apparatus of claim 11 wherein said gel delivery controller further comprises a pump controller connected to said pump for providing regulation of said variable speed pump.

13. An apparatus for applying a gel onto a material for production of disposable undergarments, the material moving in a predetermined direction of manufacture at a predetermined rate of travel, the apparatus comprising:

a) a shoe comprising a body having a lower surface, an proximal end positioned to receive the material as the sheet travels in the predetermined direction of manufacture, and a distal end, an inlet conduit positioned within the body to receive the gel therein, a chamber connected to the inlet conduit and positioned within the body, a groove extending along the lower surface of the proximal end of the body and a plurality of spaced-apart outlet conduits each extending from said chamber to said groove so that the gel is delivered onto the material in a pattern of substantially parallel lines; and
    b) a gel delivery controller positioned in fluid communication with said shoe, for providing a variably controlled flow of the gel to said inlet conduit of said shoe, therethrough to said chamber, said plurality of spaced-apart outlet conduits, and therefrom for delivery onto the sheet of material at a rate responsive to the predetermined rate of travel of the sheet of material.

14. The apparatus of claim 13 wherein the lower surface includes a slanted portion positioned along the proximal end of the body so as to form an entrance area wherein the material is received to travel without snagging under said shoe as the material moves in the predetermined direction of manufacture.

15. The apparatus of claim 14 wherein said slanted portion of the lower surface defines a first side of a predetermined angle, and wherein said material defines a second side of the angle, the angle having an open end at the proximal end of the body of said shoe.

16. The apparatus of claim 15 wherein said predetermined angle is sufficiently wide to allow said material to be received under said shoe without snagging as the sheet of material travels in the predetermined direction of manufacture.

17. The apparatus of claim 16 wherein the predetermined angle has a range of between 5 degrees to 45 degrees.

18. The apparatus of claim 17 wherein the predetermined angle further comprises the slanted portion of said lower surface having a predetermined inclination relative to the fluidity of the gel, thereby promoting a smooth flow of the gel for delivering onto the material.

19. The apparatus of claim 16 further comprising heating means for variably and controllably heating of said shoe, to thereby convert the gel to a more fluid state for delivery onto the material.

20. The apparatus of claim 19 wherein said heating means comprises a heater for heating the body of said shoe, a temperature sensor for sensing the temperature of the body of said shoe, and a temperature controller connected to the heater and to the temperature sensor for controlling the temperature of the body of said shoe.

21. The apparatus of claim 20 wherein said heater is positioned within the body of said shoe, said heater being an electric heater and being electrically connected to said temperature controller.

22. The apparatus of claim 19 wherein said shoe further comprises a substantially horizontal portion of said lower surface, said horizontal portion extending from said slanted portion to said distal end, said horizontal portion being heated and abuttingly overlying the material traveling in the predetermined direction of production so that the more fluid state of the gel is prolonged after the gel is delivered onto the material, to thereby promote enhanced absorption of the gel by the material.

23. The apparatus of claim 22 wherein said gel delivery controller comprises a pump, to thereby allow for delivery of the gel onto the material at a volume responsive to the predetermined rate of travel of the material.

24. The apparatus of claim 23 wherein said gel delivery controller further comprises a pump controller connected to said pump for providing regulation of said pump.

25. An apparatus for applying a gel onto a material moving in a predetermined direction of manufacture at a predetermined rate of travel, the apparatus comprising:
 a) a shoe for delivering a gel in a predetermined and uniformly distributed pattern to the sheet of material, said shoe having heating means for variably and controllably heating of said shoe, to thereby convert the gel to a more fluid state for delivery onto the sheet of material; and
 b) gel delivery control means positioned in fluid communication with said shoe, for providing a variably controlled flow of the gel to said shoe and therefrom onto the sheet of material at a rate responsive to the predetermined rate of travel of the sheet of material.

26. The apparatus of claim 25 wherein said shoe has an inlet conduit for receiving the gel therein, a chamber connected to said inlet conduit for distributing said gel, a plurality of spaced-apart outlet conduits each extending from said chamber so that the gel is delivered therefrom onto the sheet of material in a pattern of substantially parallel lines.

27. The apparatus of claim 26 wherein said shoe has a lower surface and a groove extending along said lower surface, said plurality of spaced-apart outlet conduits extending from said chamber to said groove for delivering said gel therefrom.

28. The apparatus of claim 27 wherein said shoe has a proximal end positioned to receive the sheet of material as the sheet travels in the predetermined direction of manufacture and a distal end positioned to discharge the sheet of material as the sheet travels in the predetermined direction of manufacture.

29. The apparatus of claim 28 wherein the lower surface includes a slanted portion positioned along the proximal end of said shoe so as to form an entrance area wherein the sheet of material is received to travel without snagging under said shoe as the sheet of material moves in the predetermined direction of manufacture.

30. The apparatus of claim 29 wherein said slanted portion of the lower surface defines a first side of a predetermined angle, and wherein said sheet of material defines a second side of the angle, the angle having an open end at the proximal end of said shoe.

31. The apparatus of claim 30 wherein said predetermined angle is sufficiently wide to allow said sheet of material to be received under said shoe without snagging as the sheet of material travels in the predetermined direction of manufacture.

32. The apparatus of claim 31 wherein the predetermined angle has a range of between 5 degrees to 45 degrees.

33. The apparatus of claim 32 wherein the predetermined angle further comprises the slanted portion of said lower surface having a predetermined inclination relative to the fluidity of the gel, thereby promoting a smooth flow of the gel for delivering onto said sheet of material.

34. The apparatus of claim 25 wherein said heating means comprises a heater for heating said shoe, a temperature sensor for sensing the temperature of said shoe, and a temperature controller connected to the heater and to the temperature sensor for controlling the temperature of said shoe.

35. The apparatus of claim 34 wherein said heater comprises an electric heater electrically connected to the temperature controller.

36. The apparatus of claim 35 wherein said shoe further comprises a substantially horizontal portion of said lower surface, said horizontal portion extending from said slanted portion to said distal end, said horizontal portion being heated and abuttingly overlying the sheet of material traveling in the predetermined direction of production so that the more fluid state of the gel is prolonged after the gel is delivered onto the sheet, to thereby promote enhanced absorption of the gel by the material.

37. The apparatus of claim 36 wherein said gel delivering control means comprises a variable speed pump, to thereby allow for delivery of the gel onto the sheet of material at a volume responsive to the predetermined rate of travel of the sheet of material.

38. The apparatus of claim 37 wherein the gel delivering control means further comprises a pump controller connected to said pump for providing regulation of the variable speed pump.

39. A shoe for delivering a gel onto a sheet of material moving in a predetermined direction of manufacture at a predetermined rate of travel, said shoe comprising:
 a) a body; and
 b) delivering means positioned within said body, said delivering means having an inlet conduit for receiving the gel therein, a chamber connected to said inlet conduit for distributing said gel, a plurality of spaced-apart outlet conduits each extending from said chamber for delivering the gel therefrom onto the sheet of material in a pattern of substantially parallel lines;
wherein said shoe body comprises a lower surface and a groove extending along said lower surface, said plurality of spaced-apart outlet conduits extending from said chamber to said groove for delivering said gel therefrom.

40. The shoe of claim 39 further comprising a proximal end positioned to receive the sheet of material as the sheet travels in the predetermined direction of manufacture and a distal end positioned to discharge the sheet of material as the sheet travels in the predetermined direction of manufacture.

41. The shoe of claim 40 wherein the lower surface includes a slanted portion positioned along the proximal end of said shoe so as to form an entrance area wherein the sheet of material is received to travel without snagging under said shoe as the sheet of material moves in the predetermined direction of manufacture.

42. The shoe of claim 41 wherein said slanted portion of the lower surface defines a first side of a predetermined angle, and wherein said sheet of material defines a second side of the angle, the angle having an open end at the proximal end of said shoe.

43. The shoe of claim 42 wherein said predetermined angle is sufficiently wide to allow said sheet of material to be received under said shoe without snagging as the sheet of material travels in the predetermined direction of manufacture.

44. The shoe of claim 43 wherein the predetermined angle has a range of between 5 degrees to 45 degrees.

45. The shoe of claim 44 wherein the predetermined angle further comprises the slanted portion of said lower surface having a predetermined inclination relative to the fluidity of the gel, thereby promoting a smooth flow of the gel for delivering onto said sheet of material.

46. The shoe of claim 43 further comprising heating means for variably and controllably heating of said shoe, to thereby convert the gel to a more fluid state for delivery onto the sheet of material.

47. The shoe of claim 46 wherein said heating means comprises a heater for heating said shoe, a temperature sensor for sensing the temperature of said shoe, and a temperature controller connected to the heater and to the temperature sensor for controlling the temperature of said shoe.

48. The shoe of claim 47 wherein said heater is positioned within said shoe, said heater being an electric heater and being electrically connected to said temperature controller.

49. The shoe of claim 46 further comprising a substantially horizontal portion of said lower surface, said horizontal portion extending from said slanted portion to said distal end, said horizontal portion being heated and abuttingly overlying the sheet of material traveling in the predetermined direction of production so that the more fluid state of the gel is prolonged after the gel is delivered onto the sheet, to thereby promote enhanced absorption of the gel by the material.

50. The shoe of claim 49 wherein said delivery controller comprises a variable speed pump, to thereby allow for delivery of the gel onto the sheet of material at a volume responsive to the predetermined rate of travel of the sheet of material.

51. The shoe of claim 50 wherein said delivery controller further comprises a pump controller connected to said pump for providing regulation of said variable speed pump.

* * * * *